US00PP22033P2

(12) United States Plant Patent
Deuter

(10) Patent No.: US PP22,033 P2
(45) Date of Patent: Jul. 19, 2011

(54) ***MISCANTHUS* PLANT NAMED 'MBS 7001'**

(50) Latin Name: *Miscanthus* spp.
Varietal Denomination: MBS 7001

(75) Inventor: Martin Deuter, Wanzleben (DE)

(73) Assignee: Mendel Biotechnology, Inc., Hayward, CA (US)

( * ) Notice: Subject to any disclaimer, the term of this patent is extended or adjusted under 35 U.S.C. 154(b) by 0 days.

(21) Appl. No.: 12/387,444

(22) Filed: May 1, 2009

Related U.S. Application Data

(60) Provisional application No. 61/050,162, filed on May 2, 2008.

(51) Int. Cl.
*A01H 5/00* (2006.01)

(52) U.S. Cl. ..... Plt./184

(58) Field of Classification Search ..... Plt./384
See application file for complete search history.

(56) References Cited

OTHER PUBLICATIONS

Münnich, C., and Jakob, K. (Nov. 27, 2008). *Miscanthus*—Breeding at Tinplant for US market, Int. *Miscanthus*-Tagung vom Nov. 27-28, 2008 in der Schweiz (International *Miscanthus* meeting of Nov. 27-28, 2008, Switzerland) (File: poster_Nov2008.pdf).

Zhang, J. (Apr. 26-27, 2007) "Lignocellulosic Feedstock Improvement", at the "Fueling Change With Renewable Energy" symposium, University of Illinois at Urbana-Champaign (File: Zhang_ Talk_ 2007.pdf).

"'Nagara' eine neue *Miscanthus*-Sorte für die Biomassegewinnung" ("Nagara, a new *Miscanthus* variety for biomass production"; Apr. 9, 2008) Tinplant biotechnik und Pflanzenvermehrung GmbH, website (File: NagaraWebpage_Apr2008.pdf). Leaflet created in and distributed from Aug. 2007.

Gutterson, N. (Aug. 19, 2008) "Bottlenecks in Feedstock Production: Can Biotechnology Address These?", at the International Conference for on Sorghum for Biofuels, Aug. 19-22, 2008, Houston Texas; (File: Gutterson_Talk_2008.pdf.

Gutterson, N. (Jan. 17, 2008) "Plant Biotechnology and Cellulosic Ethanlo Production",at the "Second Decade of Crop Biotechnology" Farm Foundation Conference, Jan. 17-18, 2008, Washington, D.C.; (File: Gutterson_Talk2_2008.pdf).

Ivanic, R. (May 19, 2009) "*Miscanthus* Potential for Second Generation Biofuels", at the 2nd Generation Biofuels Symposium, West Lafayette, IN, May 19, 2009 (File: Ivanic_Talk_2009.pdf).

Allen, D. (Jan. 10, 2008) "Genetic Improvement at Mendel Biotechnology", at the 5th annual SRI Symposium "*Miscanthus* at the University of Illinois" (File: Allen_Talk_2008.pdf).

Pude, R. *Miscanthus* International Meeting in Trier, Germany (Nov. 7-8, 2006) www.miscanthus.de/texte/Pressebericht2006.htm (File: PressReleaseIntlMeeting.pdf). Nagar and Amuri varieties introduced, order forms distributed.

*Primary Examiner* — Susan B McCormick Ewoldt
(74) *Attorney, Agent, or Firm* — Cooley LLP

(57) ABSTRACT

A new and distinct cultivar of *Miscanthus* plant named 'MBS 7001', characterized by its rigorous growth rate, top leaf height of about 2.7 meters, green-colored leaves, high biomass yield and high tiller density.

3 Drawing Sheets

Latin name of genus and species: *Miscanthus* spp.
Varietal denomination: 'MBS 7001'.

BACKGROUND

The present disclosure relates to a new and distinct cultivar of hybrid *Miscanthus* originated as a cross from *Miscanthus sacchariflorus* (♀, 4n)×*M. sinensis* (♂, 2n) plants and will be referred to hereafter by its cultivar name, 'MBS 7001.' 'MBS 700' represents a new cultivar of *Miscanthus* species, a perennial grass which is grown for biomass production, landscape use and ornamental value.

'MBS 7001', also known as 'Nagara', was selected for its vigorous growth from a selection field which was established from seedlings. The seedlings were obtained from seeds of a polycross of *Miscanthus sacchariflorus* (♀, 4n) and *M. sinensis* (♂, 2n) plants. 'MBS 7001' is a sterile triploid plant; hence, it cannot be reproduced sexually. 'MBS 7001' was generated by crossing a single large-stemmed *M. sacchariflorus* genotype from Japan (accession No.: 93M0005064, ploidy: 4x) as a female parent with a population of 15 *M. sinensis* plants as pollen donors (accession Nos.: 93m0146002, 92M0179020, 92M0179017, 93M0147009, 92M0179016, 93m0146012, 93M0144001, 93m0146017, 92m0086, 92m0179015, 93m0146001, 93M0084, 93m0006005, 93M0006003, and 93m0007212; ploidy: 2x). From this cross, 158 seedlings were obtained and planted in a field. Based on field observations, one triploid variety having high biomass was selected and designated as 'MBS 7001'.

'MBS 7001' of the present application is an about 95% to 100% sterile genotype, and is almost completely self and cross incompatible. *Miscanthus* variety 'MBS 7002' disclosed in the co-pending U.S. Plant patent application Ser. No. 12/387,429 is 100% fertile, and is about 95% to 100% self incompatible, and 95% to 100% cross compatible. *Miscanthus* variety 'MBS 1002' disclosed in the co-pending U.S. Plant patent application Ser. No. 12/584,496 is 100% fertile, and is about 95% to 100% self incompatible, and 95% to 100% cross compatible.

The plant was asexually reproduced from sterile rhizome buds in Klein-Wanzleben, Germany by the inventor. The shoot material was propagated on rooting media and the rooted plantlets were planted into pots in the greenhouse. The plants were planted into the field after one cold period. The characteristics of this cultivar have been determined to be stable and are reproduced true to type in successive generations.

SUMMARY

The following traits have been repeatedly observed and represent the characteristics of the new cultivar. Plants for the botanical measurements in the present application are two and three-year-old plants. These plants would be considered as mature plants. The phenotype may vary somewhat with variations in temperature, day-length, light intensity, soil types, and water and fertility levels without, however, any variance in genotype.

The following traits have been repeatedly observed and are determined the basic characteristics of 'MBS 7001', which in combination distinguish this *Miscanthus* hybrid from the known *Miscanthus*×*giganteus* and other ornamental *M. sinensis* forms.

1. Vigorous growth
2. Top leaf height about 2.7 meters
3. Green leaves, no colored stripes are present
4. High biomass yield (about 20-33 dry tonnes/hectare)
5. High tiller density
6. Less biomass loss in drought than *M.*×*giganteus*

'MBS 7001' can be distinguished from the *Miscanthus* cultivars Strictus (not patented), Super Stripe (U.S. Plant Pat. No. 18,161), Gold Bar (U.S. Plant Pat. No. 15,193), Little Zebra (U.S. Plant Pat. No. 13,008) and Mysterious Maiden (U.S. Plant Pat. No. 16,197) in that 'MBS 7001' has no stripes or colored bands on its leaves.

In side by side comparisons conducted in Klein-Wanzleben, Germany, 'MBS 7001' is more vigorous than either of its parent plants and produces more biomass than either parent. Plant height of 'MBS 7001' is about 20-30 cm larger than that of the *M. sacchariflorus* and *M. sinensis* parents. 'MBS 7001' has taller culms but demonstrates less lodging; hence it has stronger culms. It is late ripening and shows excellent winter survival. The leaves stay longer on top of the culm compared to *M.*×*giganteus* and, therefore, the leaf loss during the winter is minimized which, in turn, leads to equal or higher biomass yield. At spring harvest, 'MBS 7001' has lower or similar dry matter content than *M.*×*giganteus*. 'MBS 7001' produces dry matter biomass yield of 20-30 t/ha. 'MBS 7001' is sterile and produces no panicles as observed at the location in Germany.

The plant rhizome grows relatively fast and is able to cover the area between the plants within a short time. The tuft remains filled with culms compared to *M.*×*giganteus,* where the culm number in the inner tuft circle is reduced over time. The tuft diameter is around 100 cm in year 7, which is larger than that of *M.*×*giganteus* and *M. sinensis*.

The plant can be propagated by rhizomes, from meristem or nodes. This further distinguishes 'MBS 7001' from *M. sinensis* in that *M. sinensis* cannot be propagated by nodes.

BRIEF DESCRIPTION OF THE DRAWINGS

The accompanying color photographs illustrate the overall appearance and distinct characteristics of the new *Miscanthus* cultivar 'MBS 7001'.

The photograph in FIG. 1 was taken in mid-August, 2008 in Leamington, Ontario, Canada, and illustrates the overall growth habit and appearance of 'MBS 7001' eight weeks after transplanting from greenhouse-grown plants established in 2 gallon pots in a greenhouse and grown.

Figure 1:
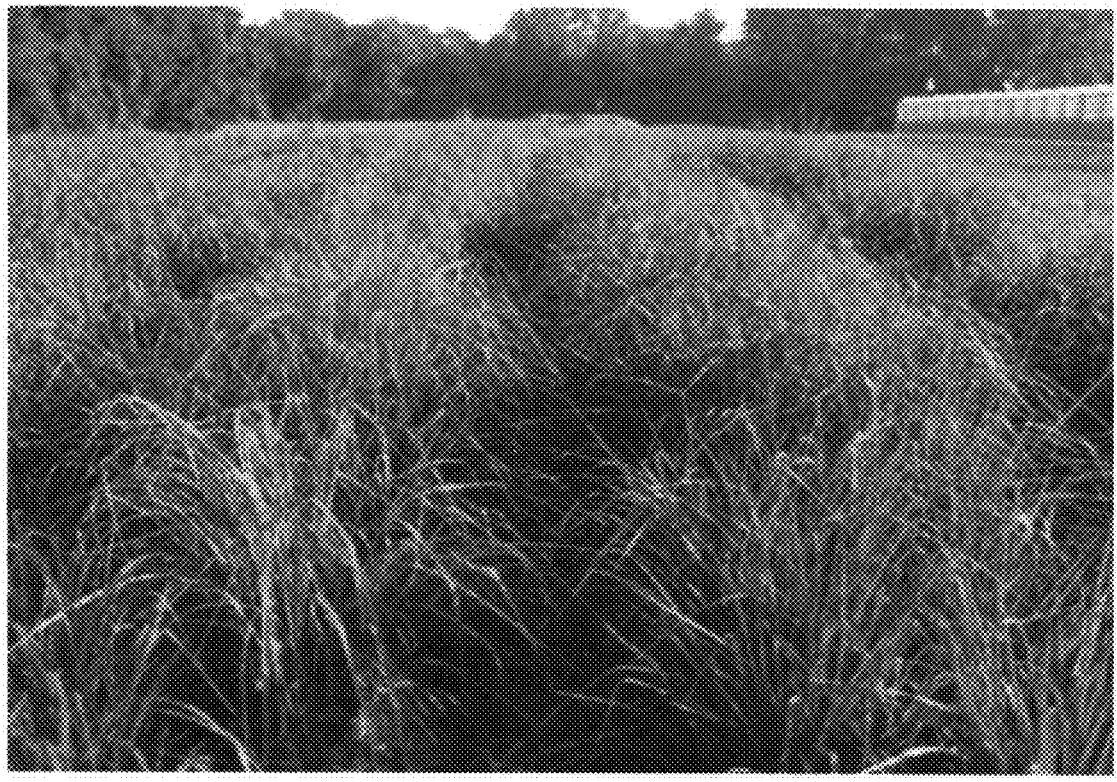
Figure 2:
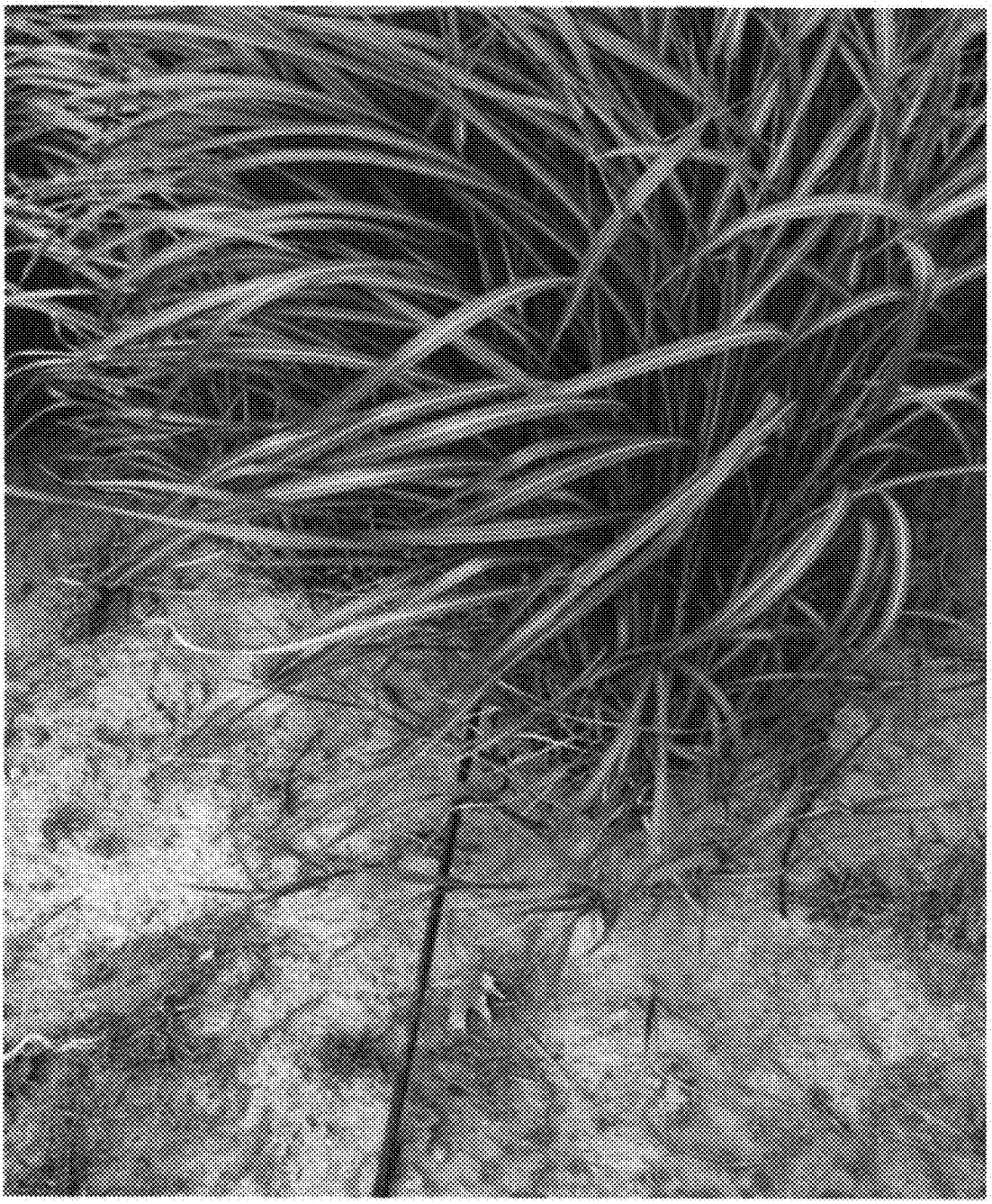

The photograph in FIG. 2 shows 'MBS 7001' growing in Leamington, Ontario, Canada, and illustrates new shoots emerging from rhizomes near the base of the main clump of tillers, and erect, flat to slightly concave leaf blades.

Figure 3:
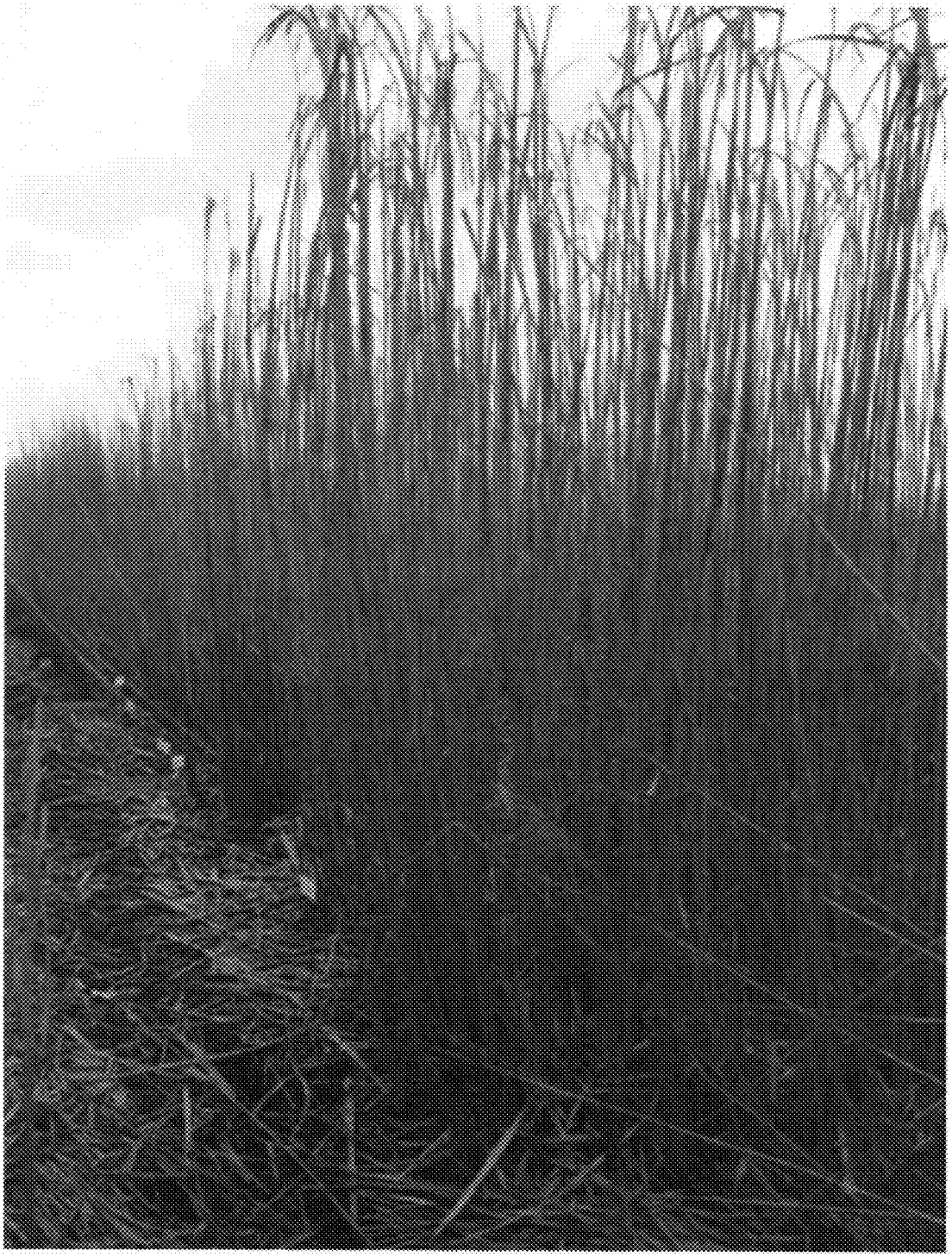

The photograph in FIG. 3 was taken in late fall, 2008 and illustrates the overall growth habit and appearance of 'MBS 7001' in Klein-Wanzleben, Germany as grown outdoors for 8 years. The 'MBS 7001' plants in the photo were harvested by removing above-ground biomass to above several inches above ground level every year for 7 years, and that the biomass visible in this photograph represents annual, rather than cumulative, growth.

DETAILED BOTANICAL DESCRIPTION OF THE PLANT

The following observations, measurements, and comparison describe this plant as grown at Klein-Wanzleben, Germany, when grown in the field. 'MBS 7001' has not been observed under all possible environmental conditions, and the phenotype may vary significantly with variations in environment. All observations were recorded during the plant's dormant season (April 2008) and during the growing season 2008 unless otherwise noted. The color determination is in accordance with The 1995 R.H.S. Colour Chart of The Royal Horticultural Society, London, England, except where general color terms of ordinary dictionary significance are used. Plants for the botanical measurements in the present application are two and three-year-old plants. These plants would be considered as mature plants.

Botanical classification: 'MBS 7001' is a sterile hybrid of a cross from *Miscanthus sinensis* and *Miscanthus sacchariflorus*

Common name: Maiden grass

Parentage: Polycross of *M. sacchariflorus* from Japan and several *M. sinensis* selected in Europe (and originated from Europe and Japan).

General description:

*Blooming period.*—Occasional inflorescence on 'MBS 7001' at Klein Wanzleben, Germany from 2001-2008. 'MBS 7001' blooms during early to late Fall. Blooming duration is about two to three weeks depending on temperature, day length, and water availability during the growing season. Blooming occurs later in the fall at northern latitudes. For example, 'MBS 7001' blooms in early to late November in Klein-Wanzleben, Germany, and early to late October in South Georgia, USA.

*Plant habit.*—Herbaceous, tuft forming, biomass grass with upright culms.

*Height and spread.*—Top leaf height about 2.7 meters. From harvest after the 2007 growing season to the spring of 2008, top leaf height was about 2.5 meters, and reached about 2.7 meters at the end of 2008). Culms can spread at the base up to 2 meters in 7 years growing time. Table 1 below shows basal circumference comparisons for 'MBS 7001' and *M.*×*giganteus* 'Illinois'.

TABLE 1

2009 Average Basal Circumference comparisons (cm) for *M. x giganteus* 'Illinois' and 'MBS 7001'

| Entry | Elora, ON | Kemptville, ON | Leamington, ON | Entry Means |
|---|---|---|---|---|
| *M. x giganteus* 'Illinois' | 94 | 59 | 94 | 83 |
| 'MBS 7001' | 105 | 65 | 115 | 95 |
| Location Means | 101 | 64 | 105 | 90 |

*Data from 2 year old mature plants

*Hardiness.*—Productive growth in Klein-Wanzleben (north central), Germany and Ontario, Canada. Less leaf loss during winter in Klein-Wanzleben, Germany than observed with *M. giganteus* growing in the same area.

*Culture.*—Grows best in sandy loam, well-drained soil in full sun. Higher yields in warmer climates and higher soil fertility, good drought resistance. Tolerant to wind and partial shade. Good stability; somewhat less tolerant to lodging than parents. Late maturing; harvest time March to April in Klein-Wanzleben, Germany. Biomass yield of about 20-33 tonnes per hectare (8-10 tons per acre). High tiller density; aboveground biomass per unit area was about 0.21, which is about the same as for *M.×giganteus*. Less biomass loss than observed for *M.×giganteus* in period of prolonged water deprivation.

*Diseases and pests.*—In United States 'MBS 7001' has shown excellent resistance to lesser stem borer spp. when compared to the public check variety *M.×giganteus* cv. Illinois clone. Observations and confirmation on stem borer tolerance occurred during early growth stages within 2-8 weeks after field planting of seedling material. This has been observed across at least 7 locations, particularly in southeastern US.

*Root description.*—Fibrous, well branched and dense. Fast-developing creeping rhizomes, with shoots arising 5-10 cm from base of the culms.

Growth and propagation:

*Propagation.*—By culm division, meristem or auxilliary buds (nodes) and in vitro culture. One method for propagation of 'MBS 7001' from in vitro culture includes the following steps: rhizomes may be harvested in the spring, the rhizomes are surface sterilized with several sterilization and wash steps, the rhizome buds are placed onto growth media until shoots develop, the shoots are transferred onto rooting media, the plantlets are transferred into soil, overwintered, and then planted in controlled conditions or in the field. 'MBS 7001' may also be propagated by rhizome division. Preferably, rhizomes may be harvested from dormant 'MBS 7001' plants in late winter before the shoots appear. To propagate 'MBS 7001' in the field, rhizomes of about 10 to 15 cm in length and weighing about 40 to 60 grams may be planted approximately 10 cm deep and approximately 1 meter apart within rows and about 1 meter between rows. Ideal planting time varies by location but good success may be achieved by planting in mid-April through May in many regions. 'MBS 7001' is a sterile triploid, and rarely flowers in temperate climates.

*Growth rate.*—Vigorous.

Culm (stem) description:

*General.*—Cylindrical, pithy, reed-like, erect.

*Culm aspect.*—Rigid and held erect, none are cascading.

*Culm color.*—Midsummer color is green to dark green (RHS 144A-146C) in Germany and the US; end of season is brown (RHS 166C-173D) in Germany and at lower latitudes in the US—Lafayette, Ind. to Southern GA the end of season range is RHS 164B at culm base to 162D at culm top past final node; lower internodes predominantly red-pink to violet (RHS N77B) with some green (RHS 144A-146C), and vary with intensity depending on locations and growing conditions. The rate on which the culm color changes is dependent on location and growing conditions. The change from green to dormancy brown as described is more rapid in the northern latitudes as in Germany when the days become increasingly shorter compared to US latitudes which impose a longer dormancy period. The culm colors at the two regions are assigned to the same color code, but with distinctive intensity.

*Culm size.*—Average about 0.69 cm in diameter, up to about 1.5 cm in diameter, and up to about 2.1 meters in height on mature plants.

*Culm surface.*—Culm is covered with hairs.

*Internode length.*—Varies from about 3 to 21 cm. Internode length decreases from the base to the apex of the culm.

*Ligule.*—Membranous, about 2.5 mm (*M.×giganteus* is 2.5-3mm), reddish in color 59B, longest hair is 2 mm (*giganteus* is 1 mm), encircles the entire culm, inner surface is glabrous, hairs on the outer surface, long hairs are mainly on the side, hairs on the side are approximately 1 mm (*M.×giganteus* is 4-5 mm).

*Culm length.*—The average culm length of 'MBS 7001' compared to *M.×gigantues* cv. 'Illinois' is shown below in Table 2.

TABLE 2

Average Culm Length comparisons (cm)

| Entry | Elora, ON | Kemptville, ON | Leamington, ON | Entry Mean |
|---|---|---|---|---|
| *M. x giganteus* 'Illinois' | 159 | 103 | 226 | 162 |
| 'MBS 7001' | 199 | 89 | 266 | 185 |
| Location Means | 179 | 96 | 246 | 174 |

*Data from 2 year old mature plants

Foliage description:

*Leaf shape.*—Linear.

*Leaf base.*—Sheathed.

*Leaf division.*—Simple.

*Leaf apex.*—Acuminate.

*Leaf aspect.*—Erect, blades are flat to slightly concave, leaf angle younger leaves 60°, leaf angle older leaves 5°.

*Leaf tip younger leaves.*—⅔ pendently, meaning approximately two thirds of the leaf tip area of the younger leaves bend downward.

*Leaf venation.*—Parallel, upper surface concave, lower surface convex, color upper surface whitish in color, code RHS N155B, rippled venation aspect compared to leaf surface.

*Leaf margins.*—Visible, sharp short bristles under the microscope.

*Leaf size.*—Up to 80 cm, width: 2-3 cm.

*Leaf persistence.*—Foliage dries and stays mostly on the stem during winter.

*Leaf attachment.*—Sheathed.

*Leaf arrangement.*—Alternate, tapering.

*Leaf surface.*—Upper-light glossy, lower-matte.

*Leaf color (during growing season).*—Relatively uniform green with no stripes, generally RHS 137A but ranging between RHS 137A to RHS 144A (*M.×giganteus* generally ranges from RHS 144A to RHS 146A). The color ranges described herein represent color changes over time. No hairs on lower leaf surface.

Flower and reproductive organ description:

*General description.*—'MBS 7001' rarely flowers in Klein-Wanzleben, Germany or Ontario, Canada. 'MBS 7001' flowers in the US. It flowers earlier in the southern regions of US September to Oct., and October to November in the northern regions of US. Seed is very rarely produced. Less than 2%, usually 0% panicles of 'MBS 7001' produce seed.

Panicle color: Varies from 152D-176B. The intensity of these color grades depends on location and growing conditions. However, this color report indicates that 176B would be early panicle appearance and 152D is for mature panicle appearance.

Yield: The average yield of 'MBS 7001' compared to *M.×gigantues* cv. 'Illinois' is shown below in Table 3.

TABLE 3

Average Yield (tons/ac) comparisons in Canada*

| Material Name | Leamington | Elora | Entry Mean |
|---|---|---|---|
| 'MBS 7001' | 3.0 | 8.4 | 5.7 |
| *M. x giganteus* 'Illinois' | 1.7 | 4.5 | 3.1 |
| Location Means | 2.4 | 6.1 | 4.3 |
| Lsd 0.05 | 1.3 | 2.8 | 1.8 |

*Data from 2 year old mature plants

Moisture: The average moisture of 'MBS 7001' compared to *M.×gigantues* cv. 'Illinois' is shown below in Table 4.

TABLE 4

Average % Moisture comparisons in Canada*

| Material Name | Leamington | Elora | Entry Mean |
|---|---|---|---|
| 'MBS 7001' | 29 | 41 | 35 |
| *M. x giganteus* 'Illinois' | 36 | 48 | 42 |
| Location Means | 33 | 45 | 39 |
| Lsd 0.05 | 2.3 | 3.8 | 3.2 |

*Data from 2 year old mature plants

*M.×giganteus* is also a cross between *M. saccharafloris* (4x) and *M. sinensis* (2x) resulting in a sterile clone plant selection that is available to the public. This is how 'MBS 7001' was derived, only using different parentage in the ploycross as described. Therefore *M.×giganteus* (3x) cv 'Illinois clone' is an excellent cultivar for comparison with 'MBS 7001'. In this comparison 'MBS 7001' is slightly greener during the growing season than *M.×giganteus* across locations.

The invention claimed is:

1. A new and distinct cultivar of *Miscanthus* plant named 'MBS 7001' substantially as herein shown and described.

* * * * *